United States Patent [19] [11] 4,208,426
Minami et al. [45] Jun. 17, 1980

[54] PYRANOCHROMONE DERIVATIVES AND THERAPEUTIC COMPOSITION COMPRISING SAME FOR TREATMENT OF ALLERGIC DISEASES

[75] Inventors: Norio Minami, Kamakura; Shizumasa Kijima; Satoshi Katayama, both of Tokyo; Hiroshi Shionoya, Tokorozawa, all of Japan

[73] Assignee: Eisai Co., Ltd., Tokyo, Japan

[21] Appl. No.: 927,044

[22] Filed: Jul. 24, 1978

[30] Foreign Application Priority Data

Jul. 28, 1977 [JP] Japan .................................. 52-89765

[51] Int. Cl.² ..................... A61K 31/35; C07D 311/78
[52] U.S. Cl. .................................. 424/283; 260/345.2
[58] Field of Search ...................... 260/345.2; 424/283

[56] References Cited

U.S. PATENT DOCUMENTS 3,629,290 12/1971 Cairns et al. ...................... 260/345.2
3,952,013 4/1976 Hazard et al. ..................... 260/345.2

FOREIGN PATENT DOCUMENTS 51-76277 7/1976 Japan .................................... 260/345.2
1517153 7/1978 United Kingdom .................. 260/345.2

Primary Examiner—Nicky Chan
Attorney, Agent, or Firm—Wenderoth, Lind & Ponack

[57] ABSTRACT

Novel pyranochromone derivatives having the general formula:

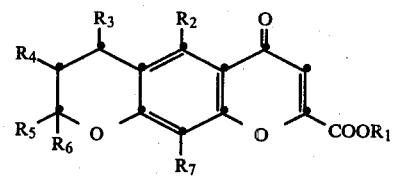

wherein $R_1$ represents hydrogen atom, an alkali metal or an alkyl group containing 1–4 carbon atoms; $R_2$, $R_3$ and $R_4$ represent hydrogen atom or an alkyl group containing 1–4 carbon atoms respectively, provided that both $R_3$ and $R_4$ are not hydrogen atom at the same time; $R_5$ and $R_6$ represent an alkyl group containing 1–4 carbon atoms respectively; and $R_7$ represents hydrogen atom, hydroxyl group, an alkyl group containing 1–4 carbon atoms or an alkoxyl group containing 1–4 carbon atoms. The novel medicaments comprising predominantly the above derivative are effective for the treatment of allergic diseases.

28 Claims, No Drawings

PYRANOCHROMONE DERIVATIVES AND THERAPEUTIC COMPOSITION COMPRISING SAME FOR TREATMENT OF ALLERGIC DISEASES

This invention relates to novel pyranochromone derivatives having the general formula:

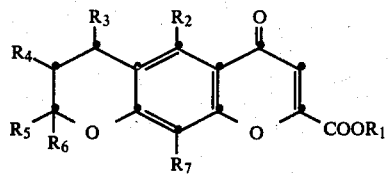
(I)

wherein $R_1$ represents hydrogen atom, an alkali metal or an alkyl group containing 1-4 carbon atoms; $R_2$, $R_3$ and $R_4$ represent hydrogen atom or an alkyl group containing 1-4 carbon atoms respectively, provided that both $R_3$ and $R_4$ are not hydrogen atom at the same time; $R_5$ and $R_6$ represent an alkyl group containing 1-4 carbon atoms respectively; and $R_7$ represents hydrogen atom, hydroxyl group, an alkyl group containing 1-4 carbon atoms or an alkoxyl group containing 1-4 carbon atoms, and novel therapeutic compositions for the treatment of allergic disease comprising said derivatives.

For the treatment of allergic disease due to the antigen-antibody reaction, there are conventionally used anti-histaminics and anti-serotonic medicaments and the like having the antagonistic activity to histamine and serotonin and the like which are the chemical mediators of the allergic disease. However, it can not be said that the effect of said single antagonistic covers over all chemical mediators. And, there are many ineffective examples regarding patients suffering from allergic diseases such as, particularly asthma. Moreover, these antagonistics are often accompanied with adverse effects such as the hypnotic effect and the inhibition of bronchial secretion.

There has been recently developed, as non-antagonistic, cromoglycate which is a derivative of chromone and is believed to have inhibiting effect on the release of the chemical mediators. However, cromoglycate is not effective when it is orally administered, and it is therefore limited to an inhalation administration. Thus, an inhaler is required for such inhalation administration, whereby its handling is inconvenient.

Japanese Patent Application Laid-open No. 76,277/76 discloses pyranochromone derivatives which are considered as the medicaments of the same series of cromoglycate. However, the effect of said compounds are also comparatively low in the case of oral administration.

The novel pyranochromone derivatives of the formula I according to this invention are believed to show the anti-allergic effect in accordance with the same function mechanism as that of cromoglycate. They are however characterized by an excellent effect on oral administration.

Various processes may be considered, for the preparation of the compounds according to this invention, depending on their chemical structures. The illustrative processes are as follows:

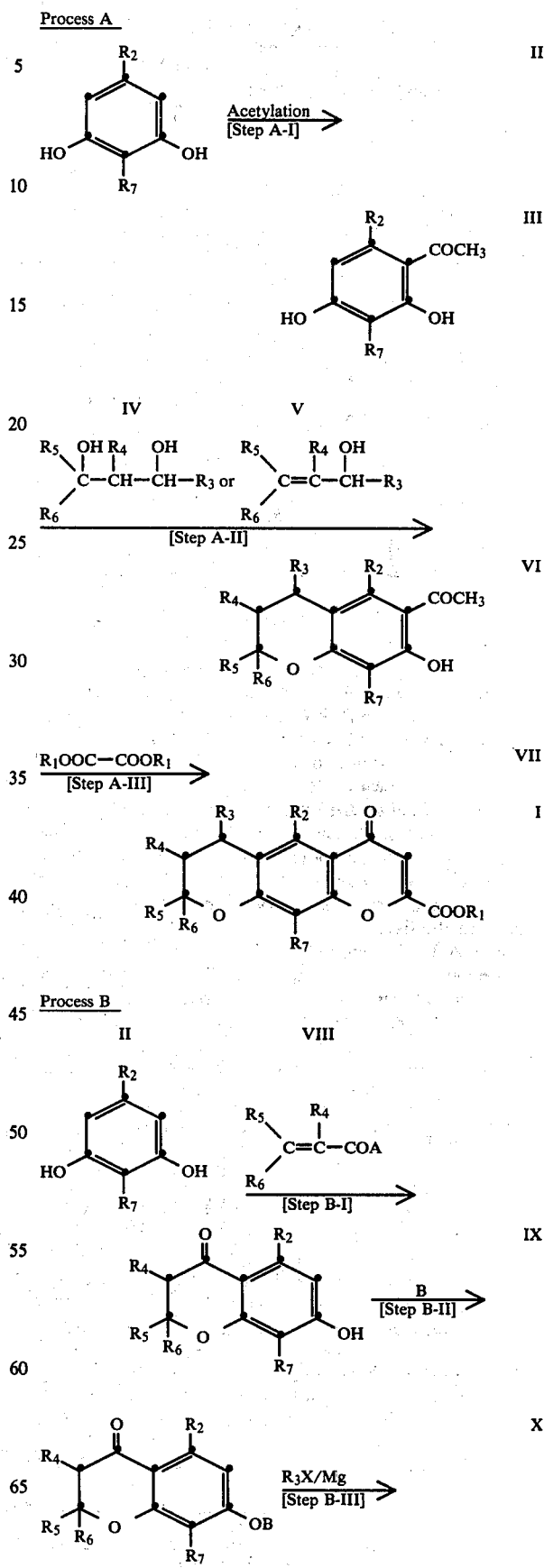

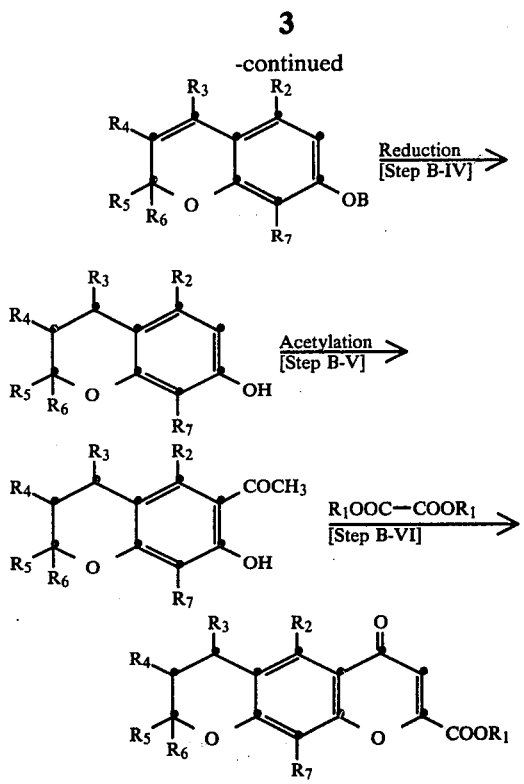

In the foregoing formulae, $R_1$–$R_7$ have the same meaning as defined above; A represents a halogen atom or hydroxyl group; B represents a protective group for hydroxyl group; and X represents a halogen atom.

Step A-1: Compound III is produced by reacting Compound II with acetic anhydride, acetic acid chloride, acetic acid or the like, using an acid catalyst such as aluminum chloride, zinc chloride, titanium tetrachloride, stannic chloride, boron trifluoride and the like, in the presence or absence of a solvent such as dichloromethane, nitrobenzene, carbon tetrachloride, acetic acid and the like.

Step A-II: Compound VI is produced by reacting Compound III with Compound IV or Compound V, using an acid catalyst such as sulfuric acid, aluminum chloride, boron trifluoride, oxalic acid, phosphoric acid and the like, in a solvent such as ethyl ether, isopropyl ether, dichloromethane, ethyl acetate and the like, at a temperature ranging from room temperature to a reflux temperature.

Step A-III: Object compound I is produced by reacting a dialkyl oxalate of Compound VII with Compound VI in a solvent such as alcohol and the like in the presence of an alkali such as sodium alcolate and the like, followed by heating the resulting reaction product with alcohol solvent containing an acid such as hydrochloric acid and the like. When the object compound is a corresponding free carboxylic acid or a salt of carboxylic acid, Compound I may be produced by making at first it in a form of the corresponding carboxylate, and then hydrolizing the carboxylate.

The foregoing is an explanation of the process A. The acetylation of the step A-1 and the condensation of the step A-II may be changed in the reverse order. Such reverse process is preferable in the case of synthesis of Compound I wherein both $R_2$ and $R_7$ are not hydrogen atom at the same time.

Step B-I: Compound IX is produced by reacting Compound II with Compound VIII, using an acid calalyst such as aluminum chloride, zinc chloride, titanium tetrachloride, boron trifluoride, polyphosphoric acid and the like, in a solvent such as dichloromethane, nitrobenzen, ether and the like.

Step B-II: Compound X is produced by reacting Compound IX with a protecting material for hydroxyl group such as benzylbromide, allylbromide and the like, using an alkali such as potassium carbonate and the like, in a solvent such as dimethyl formamide, acetone, methyl ethyl ketone and the like.

Step B-III: Compound XI is produced by reacting Compound X with Grignard's reagent which is prepared by reacting magnesium with a halogenated alkyl ($R_3X$) in a solvent such as ether, tetrahydrofurane and the like, followed by adding hydrochloric acid.

Step B-IV: Compound XII is produced by subjecting Compound XI to a catalytic reduction, using a catalyst for catalytic reduction such as palladium-carbon and the like.

Step B-V: Compound VI is produced by acetylating Compound XII. The acetylation is the same procedure as described in the step A-I.

Step B-VI: The step is the same as described in the step A-III.

The following are results of pharmacological experiments of the compounds according to this invention.

(1) Homologous passive cutaneous anaphylaxis (PCA) reaction

Anti-egg albumin rat serum in amount of 0.1 ml was intracutaneously injected to the shaved back of a mail rat of SD (Sprague-Dawley) strain weighing 200±30 g. The egg-albumin as antigen in amount of 5 mg/Kg were intravenously injected, together with 40 mg/Kg of dye (Evans blue) 24 hours after antiserum injection. The test materials were given at the respective times before antigen injection as 5% suspension in gum arabic in the case of oral administration (p. o.), while as a solution in physiological salt solution in the case of the intravenous injection (i. v.). The rat was sacrificed 30 minutes after the injection of the antigen, and the skin was removed. The amount of the dye leaked at the reaction locus was measured by extraction method according to Katayama et al.; Microbiol. Immunol. 22, 89–101 (1978), to determine the inhibiting rate on the homologous PCA reaction. There were elected, as the control, cromoglycate and ethyl 6,7-dihydro-6-methyl-8H-pyrano[3,2-g]chromone-2-carboxylate which are known in the art. Results are shown in Table 1.

As shown in Table 1, the compounds according to this invention exhibit the inhibiting effect on the PCA reaction, in the respective cases of the oral administration and the intravenous injection. In the case of the oral administration, the effect of the compounds according to this invention is superior to that of the control compounds.

Table I

| | Test material | Dose (mg/Kg) | Route of Administration | Time for Administration | Inhibition rate of PCA reaction (%) |
|---|---|---|---|---|---|
| | Ethyl 6,7-dihydro-6,8,8,10-tetramethyl-8H-pyrano[3,2-g]chromone-2-carboxylate | 20 | p. o. | before one hour | 63.8 |
| Compounds | Sodium 6,7-dihydro-6,8,8,10-tetramethyl- | 20 | p. o. | before one hour | 64.9 |

Table I-continued

| | Test material | Dose (mg/Kg) | Route of Administration | Time for Administration | Inhibition rate of PCA reaction (%) |
|---|---|---|---|---|---|
| according to this invention | 8H-pyrano[3,2-g]chromone-2-carboxylate | 0.4 | i. v. | at the same time | 65.2 |
| | Ethyl 6,7-dihydro-5,7,8,8,10-pentamethyl-8H-pyrano[3,2-g]chromone-2-carboxlate | 20 | p. o. before one hour | | 47.9 |
| | Ethyl 6,7-dihydro-10-methoxy-6,8,8-trimethyl-8H-pyrano[3,2-g]chromone-2-carboxylate | 20 | p. o. | before one hour | 62.2 |
| | Ethyl 6,7-dihydro-10-ethyl-5,6,8,8-tetramethyl-8H-pyrano[3,2-g]chromone-2-carboxylate | 20 | p. o. | before one hour | 64.4 |
| Control compounds | Chromoglycate | 20 | p. o. | before one hour | 0 |
| | | 6 | i. v. | at the same time | 88.6 |
| | Ethyl 6,7-dihydro-6-methyl-8H-pyrano[3,2-g]chromone-2-carboxylate | 20 | p. 0. | before one hour | 23.7 |

Regarding 6,7-dihydro-6,8,8,10-tetramethyl-8H-pyrano[3,2-g] chromone-2-carboxylic acid of this invention, there were determined, in the same manner, inhibition effect of PCA reaction when oral administration was carried out. Table 2 shows their results. As shown in Table 2, the subject compound exhibits a dose-dependent inhibiting effect, and shows the most remarkable inhibition effect when it was administered before 15–30 minutes.

Table 2

| Dose (mg/Kg) | Time for administration | Inhibition effect of PCA reaction (%) |
|---|---|---|
| 10 | before 2 minutes | 44.1 |
| 10 | before 5 minutes | 62.2 |
| 10 | before 15 minutes | 82.0 |
| 10 | before 30 minutes | 84.3 |
| 10 | before 60 minutes | 54.3 |
| 1 | before 5 minutes | 15.1 |
| 3 | before 5 minutes | 54.8 |
| 10 | before 5 minutes | 78.5 |
| 30 | before 5 minutes | 90.3 |

(2) Histamine release from actively sensitized rat peritoneal mast cells mediated by antigen-antibody reaction A male rate of SD strain weighing 200–400 g was used in this experiment. The sensitization of rats was performed by the method according to Kusner et al.; J. Pharmcol. & Exper. Ther, 184, 41–44 (1973). The mast cells were isolated 14 days after the sensitization by the method according to Johnson, et al.; Am. J. Physiol. 216, 453–459 (1969). The number of the mast cells was adjusted to $2 \times 10^5$/ml. Each one milliliter of the cell suspension was divisionally poured into siliconized test tubes, and placed in an incubator adjusted to 37° C. The egg-albumine, as antigen, was added thereto at the final concentration of 10 μg/ml. At the same time of the addition of antigen, there is added sodium 6,7-dihydro-6,8,8,10-tetramethyl-8H-pyrano[3,2-g] chromone-2-carboxylate according to this invention in the respective concentrations.

The amount of histamine released from the mast cells was determined fluorimetrically according to Suzuki's method [Keio Igaku, 50, 263–270 (1973) Japan]. Results are shown in Table 3.

Table 3

| Concentration of the object material | Inhibition rate of histamine release |
|---|---|
| 0.2 μM | 48.2 % |
| 1.0 μM | 66.1 % |
| 2.0 μM | 73.2 % |
| 10.0 μM | 60.7 % |

As shown in Table 3, the compounds according to this invention have an inhibiting effect to the antigen-antibody mediated histamine release from rat peritoneal mast cells.

(3) Acute toxicity (For 15 days after administration)

ICR strain mouse of 7 weeks old and weighing 30±7 g were used in this experiment. In the case of the oral administration of 10,000 mg/Kg of the compound according to this invention, there was no mortal example, and not recognized any abnormality due to the medicinal poisoning in anatomical examination. In the case of the administration into the abdominal cavity, $LD_{50}$ was about 1000–1500 mg/Kg.

As clearly indicated from the results of the above pharmacological experiments, the compounds according to this invention are effective for treating the allergic diseases, for example, allergic asthma, allergic coryza, atopic dermatitis, idiopathic ulcerative colitis, urticaria and the like.

The dose of the compounds according to this invention is preferably about 1–1,000 mg and more preferably 10–100 mg per day for an adult. The forms of administration may include powder, granule, capsule, tablet, syrup, etc. These forms may be produced by conventional methods using any conventional pharmaceutically acceptable carrier such as carboxymethylcellulose, crystallized cellulose, starch, hydroxypropylcellulose, lactose, polyvinyl pyroridone, gum arabic, calcium stearate, talc, white sugar, sorbitol, etc.

The following examples will give more detailed explanation of the present invention. Percentages are by weight unless otherwise specified.

EXAMPLE 1

Ethyl 6,7-dihydro-5,6,8,8,10-pentamethyl-8H-pyrano [3,2-g] chromone-2-carboxylate (1) 7-Hydroxy-2,2,4,5,8-pentamethyl chroman 13.8 g. of 2,5-dimethyl resorcinol were dissolved in a mixed solution comprising 70 ml of isopropyl ether and 5 ml of concentrated sulfuric acid. Then, 10 g. of 4-methyl-3-pentene-2-ol were added dropwise to the solution at the temperature of about 60° C. for about 30 minutes. The resulting solution was cooled, and washed with water, with 1 N sodium hydroxide solution, and again with water and then dried over magnesium sulfate. The solvent was distilled off under reduced pressure. The residue was recrystallized from ether/n-hexane, to obtain 13.2 g. (yield: 60%) of the subject compound. Melting point: 88°–89° C.

(2) 6-Acetyl-7-hydroxy-2,2,4,5,8-pentamethyl chroman

Boron trifluoride-acetic acid complex in amount of 30 g. were added to 11 g. of the compound prepared by the procedure described in (1), and the mixture was stirred at the temperature of 60°–70° C. for 2.5 hours. Ice water was then added to the mixture. The solution was extracted with ether. The ether layer was washed with water, with 1 N sodium hydroxide solution, and again with water, then dried over magnesium sulfate. The solvent was distilled off under reduced pressure. The residue was recrystallized from ether/n-hexane, to obtain 12.0 g. (yield: 91.6%) of the subject compound. Melting point: 80°–81° C.

(3) Ethyl 6,7-dihydro-5,6,8,8,10-pentamethyl-8H-pyrano [3,2-g] chromone-2-carboxylate A sodium ethylate solution in ethanol was prepared from 2.0 g. of metallic sodium and 60 ml of ethanol. To this solution, 5.24 g. of the compound obtained in (2) were added at 40° C. Subsequently, 12 g. of diethyl oxalate were added dropwise at 50°–60° C. for 30 minutes. After reflux for one hour, the reaction solution was poured into ice water, and acidified with hydrochloric acid, then extracted with ether. The ether ws distilled off from the extract. To the residue was added ethanol containing concentrated hydrochloric acid, and the whole was refluxed for one hour. The ethanol was distilled off under reduced pressure. The residue was dissolved in ether, and washed with water, with 1 N sodium bicarbonate solution, and again with water, then dried over magnesium sulfate. The ether was distilled off under reduced pressure. The residue was recrystallized from ethanol/n-hexane. There were obtained 4.8 g. (yield: 69.7%) of the subject compound.
Melting point: 94°–95° C.
Elemental analysis of the compound having the presumed formula $C_{20}H_{24}O_5$ gave:

|  | C | H |
| --- | --- | --- |
| Calculated (%): | 69.75 | 7.02 |
| Found (%): | 69.49 | 7.17 |

Infrared spectra $\nu_{max}.^{nuj.}$ cm$^{-1}$: 1725, 1655, 1630, 1260.
Mass spectra (m/e): 344 (M+).
Nuclear magnetic resonance spectra (CDCl$_3$) δ: 1.26(s), 1.36(t), 1.50(s), 1.80(q), 2.10(q), 2.30(s), 2.78(s), 3.26(m), 6.90(s).

(4) Sodium 6,7-dihydro-5,6,8,8,10-pentamethyl-8H-pyrano [3,2-g] chromine-2-carboxylate To 1.032 g. of the compound obtained in (3), 7.5 ml of ethanol were added. Subsequently, 1 N sodium hydroxide solution was further added with stirring. The solvent was distilled off under reduced pressure. The residue was dissolved in acetone, and ether was added to said solution. The precipitates were filtered by suction and dried, to obtain 0.9 g. of the subject compound.
Melting point: over 250° C.
Infrared spectra $\nu_{max}.^{nuj.}$ cm$^{-1}$: 1630, 1580, 1140, 1125.
Elemental analysis of the compound having presumed formula $C_{18}H_{19}O_5Na$ gave:

|  | C | H |
| --- | --- | --- |
| Calculated (%): | 63.90 | 5.66 |
| Found (%): | 63.86 | 5.63 |

EXAMPLE 2

6,7-Dihydro-6,8,8,10-tetramethyl-8H-pyrano [3,2-g] chromone-2-carboxylic acid (1) 2,4-Dihydroxy-3-methylacetophenone A mixture prepared by adding 294 g. of boron trifluoride-acetic acid complex to 124 g. of 2-methyl resorcinol was stirred at 100°–105° C. for 3 hours. The reaction solution was poured into 2 l of ice water and crystals precipitated out were recovered by filtration. The crystals recovered were washed with water and recrystallized from ethanol (150 ml)/water (50 ml) to obtain 146.8 g. (yield: 88.4%) of the subject compound. Melting point: 155°–156° C.

(2) 6-Acetyl-7-hydroxy-2,2,4,8-tetramethyl chroman

Ethyl acetate in amount of 150 ml together with concentrated sulfuric acid in amount of 7.5 ml were added to 24.9 g. of the compound obtained in (1).
To this solution, 35.4 g. of 2-methylpentane-2,4-diol were added dropwise under reflux for 30 minutes. The reaction solution was cooled, then washed with water, with 1 N sodium hydroxide solution, and again with water, then dried over magnesium sulfate. The solvent was distilled off under reduced pressure. The residue was recrystallized from ether/n-hexane to obtain 31.5 g. (yield: 84.7%) of the subject compound. Melting point: 96°–97° C.

(3) Ethyl 6,7-dihydro-6,8,8,10-tetramethyl-8H-pyrano [3,2-g] chromone-2-carboxylate A solution of sodium ethylate in ethanol was prepared by adding 27.6 g. of metallic sodium to 800 ml of ethanol. To this solution, 74.4 g. of the compound obtained in (2) were added at the temperature of approximately 40° C. 175.2 g. of diethyl oxalate were added dropwise for 20 minutes maintaining said temperature. The solution was refluxed for two hours. The reaction solution was poured into the ice water (4 l)/concentrated hydrochloric acid (200 ml) solution. The yellow crystals precipitated out were recovered by filtration. The crystals were washed with water, and dissolved in the ethanol (500 ml)/concentrated hydrochloric acid (5 ml), then refluxed for one hour. The solvent was distilled off under reduced pressure. The residue was dissolved in ethyl acetate, and washed with water, with 1 N-sodium bicarbonate solution and again with water, then dried over magnesium sulfate. The ethyl acetate was distilled off. The residue was recrystallized from the ethanol/n-hexane, to obtain 61.6 g. (yield: 62.2%) of the subject compound. Melting point: 113°–114° C.

Elementary analysis of the compound having presumed formula $C_{19}H_{22}O_5$ gave:

|  | C | H |
|---|---|---|
| Calculated (%): | 69.07 | 6.71 |
| Found (%): | 68.89 | 6.78 |

Infrared spectra $\nu_{max}.^{nuj.}$ cm$^{-1}$: 1735, 1650, 1630, 1265.

Mass spectra (m/e): 330 (M+).

Nuclear magnetic resonance spectra (CDCl$_3$) δ: 1.26(s), 1.36(d), 1.44(s), 1.50–2.00(m), 2.28(s), 2.80–3.16(m), 6.98(s), 7.92(s).

(4) Sodium 6,7-dihydro-6,8,8,10-tetramethyl-8H-pyrano [3,2-g] chromone-2-carboxylate Ethanol in amount of 250 ml was added to 33 g. of the compound obtained in (3). A solution of 1 N-sodium hydroxide was added dropwise to said mixture with stirring at 15° C. After stirring for about two hours, the solvent was distilled off under reduced pressure, and the residue was dissolved in acetone. Ether was added to this solution. The precipitates were recovered by filtration and dried, to obtain 30 g. of the subject compound.

Melting point: over 250° C.

Elemental analysis of the compound having the presumed formula $C_{17}H_{17}O_5Na$ gave:

|  | C | H |
|---|---|---|
| Calculated (%): | 62.96 | 5.28 |
| Found (%): | 62.98 | 5.25 |

Infrared spectra $\nu_{max}.^{nuj.}$ cm$^{-1}$: 1630, 1600, 1140, 1120.

(5) 6,7-Dihydro-6,8,8,10-tetramethyl-8H-pyrano [3,2-g] chromone-2-carboxylate acid The compound obtained in (4) in amount of 13 g. were acidified with hydrochloric acid and extracted with ethyl acetate. The layer of ethyl acetate was washed with water and dried over magnesium sulfate. The solvent was distilled off under reduced pressure. The residue was recrystallized from the ethyl acetate/ethanol to obtain 11 g. of the subject compound.

Melting point: 286°–288° C. (with decomposition).

Elemental analysis of the compound having presumed formula $C_{17}H_{18}O_5$ gave:

|  | C | H |
|---|---|---|
| Calculated (%): | 67.54 | 6.00 |
| Found (%): | 67.41 | 5.95 |

Infrared spectra $\nu_{max}.^{nuj.}$ cm$^{-1}$: 1725, 1630, 1250.

Nuclear magnetic resonance spectra (CD$_3$OD) δ: 1.24(s), 1.44(d), 1.52(s), 2.30(s), 6.88(s), 7.88(s).

EXAMPLE 3

Ethyl 6,7-dihydro-10-methoxy-6,8,8-trimethyl-8H-pyrano [3,2-g] chromone-2-carboxylate (1) 2,3,4-Trihydroxy acetophenone A mixture was prepared from 126 g. of pyrogallol and 294 g. of boron trifluoride-acetic acid complex, and stirred at 100°–105° C. for three hours. The mixture was poured into 2 l of ice water. The crystals precipitated out were recovered by filtration, and washed with water, then recrystallized from ethanol (100 ml)/water (100 ml) solvent, to obtain 137.2 g. (yield: 81.7%) of the subject compound.

Melting point: 172°–173° C.

(2) 6-Acetyl-7,8-dihydroxy-2,2,4-trimethylchroman

A mixture was prepared from 58.8 g. of the compound obtained in (1), 350 ml of isopropyl ether and 17.5 ml of concentrated sulfuric acid. To this mixture, 82.6 g. of 2-methylpentane-2,4-diol were added dropwise with stirring under reflux for 45 minutes. The reaction solution was cooled, and washed with water, with 1 N sodium hydroxide solution and again with water, then dried over magnesium sulfate. The solvent was distilled off under reduced pressure. The residue was recrystallized from the ether/n-hexane, to obtain 77.5 g. (yield: 88.6%) of the subject compound.

Melting point: 153°–154° C.

(3) Ethyl 6,7-dihydro-10-hydroxy-6,8,8-trimethyl-8H-pyrano [3,2-g] chromone-2-carboxylate A solution of sodium ethylate in ethanol was prepared by adding 27.6 g. of metallic sodium to 800 ml of ethanol. To this solution, 50 g. of the compound obtained in (2) were added at the temperature of approximately 40° C. 120 g. of diethyl oxalate were then added dropwise at the same temperature for 20 minutes. The solution was refluxed for two hours, then, poured into ice water (4 l)/concentrated hydrochloric acid (200 ml) solution. The crystals precipitated out were recovered by filtration, washed with water, and dissolved in ethanol (500 ml)/concentrated hydrochloric acid (5 ml). The solution was refluxed for 1.5 hours. About 300 ml of ethanol were distilled off. The yellow crystals precipitated out were recovered by filtration to obtain 50.6 g. (yield: 76.2%) of the subject compound.

Melting point: 225°–226° C. (with decomposition), Mass spectrum (m/e): 332 (M+).

Elementary analysis of the compound having the presumed formula $C_{18}H_{20}O_6$ gave:

|  | C | H |
|---|---|---|
| Calculated (%): | 65.05 | 6.07 |
| Found (%): | 65.02 | 6.06 |

Infrared spectra $\nu_{max}.^{nuj.}$ cm$^{-1}$: 3200, 1745, 1645, 1625, 1140.

(4) Ethyl 6,7-dihydro-10-methoxy-6,8,8-trimethyl-8H-pyrano [3,2-g] chromone-2-carboxylate A mixture was prepared from 33.2 g. of the compound obtained in (3), 42.3 g. of methyl iodide, 41.4 g. of potassium carbonate and 400 ml of acetone, and refluxed for 3 hours, then filtered. The solvent was distilled off from the filtrate. The residue was dissolved in ether, subsequently, washed with water, with aqueous 1 N sodium bicarbonate solution and again with water, then dried over magnesium sulfate. After ether was distilled off, the residue was recrystallized from ethanol/n-hexane, to obtain 26.5 g. (yield: 76.5%) of the subject compound.

Melting point: 86°–87° C.

Elementary analysis of the compound having presumed formula $C_{19}H_{22}O_6$ gave:

|  | C | H |
|---|---|---|
| Calculated (%): | 65.88 | 6.40 |
| Found (%): | 65.88 | 6.55 |

Mass spectra (m/e): 346 (M+).

Infrared spectra $\nu_{max.}^{nuj.}$ cm$^{-1}$: 1735, 1650, 1620, 1260.

Nuclear magnetic resonance spectra (CDCl$_3$) δ: 1.32(s), 1.40(d), 1.52(s), 1.58–2.04(m), 2.88–3.20(m), 3.96(s), 7.00(s), 7.84(s)

(5) Sodium 6,7-dihydro-10-methoxy-6,8,8-trimethyl-8H-pyrano[3,2-g] chromone-2-carboxylate To 1.73 g. of the compound obtained in (4), were added 10 ml of ethanol. 5 ml Of aqueous 1 N sodium hydroxide solution were further added with stirring. Then, the same procedures described in (4) of Example 1 were repeated. There were thus obtained 1.6 g. of the subject compound.

Nuclear magnetic resonance spectra (CDCl$_3$) δ: 1.32(s), 1.38(d), 1.50(s), 1.50–2.08(m), 2.88–3.10(m), 3.92(s), 6.76(s), 7.64(s).

Melting point: over 250° C.

Elementary analysis of the compound having presumed formula $C_{17}H_{17}O_6Na$ gave:

|  | C | H |
|---|---|---|
| Calculated (%): | 60.00 | 5.03 |
| Found (%): | 60.01 | 5.00 |

Infrared spectra $\nu_{max.}^{nuj.}$ cm$^{-1}$: 1630, 1210, 1135, 1120.

EXAMPLE 4

Ethyl 6,7-dihydro-10-ethoxy-6,8,8-trimethyl-8H-pyrano[3,2-g] chromone-2-carboxylate A mixture comprising 996 mg of the compound obtained in (3) of Example 3, 468 mg of ethyl iodide, 622 mg of potassium carbonate and 50 ml of chloroform, was treated by the same procedure as described in (4) of Example 3. There were obtained 757 mg (yield: 70.0%) of the subject compound.

Melting point: 76°–77° C.

Mass spectrum (m/e): 360 (M+).

Elementary analysis of the compound having the presumed formula $C_{20}H_{24}O_6$ gave:

|  | C | H |
|---|---|---|
| Calculated (%): | 66.65 | 6.71 |
| Found (%): | 66.86 | 6.92 |

Nuclear magnetic resonance spectra (CDCl$_3$) δ: 1.30(s), 1.50(s), 1.68–2.04(m), 2.88–3.16(m), 7.00(s), 7.82(s).

EXAMPLE 5

Ethyl 6,7-dihydro-10-propyl-5,6,8,8-tetramethyl-8H-pyrano[3,2-g] chromone-2-carboxylate (1) 7-Hydroxy-8-propyl-2,2,4,5-tetramethylchroman An amount of 1.77 g. of 2-methylpentane-2,4-diol were added dropwise at the temperature of approximately 60° C. to a mixed solution prepared from 2.49 g. of 2-propyl-5-methyl resorcinol, 15 ml of isopropyl ether and 1 ml of concentrated sulfuric acid. The solution was cooled, and successively washed with water, aqueous 1 N sodium hydroxide solution, and again with water, and then dried over magnesium sulfate. The solvent was distilled off under reduced pressure. The residue was purified by subjecting to column chromatography filled with silica gel. There were thus obtained 2.7 g. (yield: 72.6%) of the subject compound in oily form.

(2) 6-Acetyl-7-hydroxy-8-propyl-2,2,4,5-tetramethylchroman

A mixture was prepared from 2.48 g. of the compound obtained in (1) and 4 g. of boron trifluoride-acetic acid complex, and subsequently stirred at 60°–70° C. for 2.5 hours. After adding ice water, the mixture was extracted with ether. The ether layer was successively washed with water, aqueous 1 N sodium hydroxide solution, and again with water, and then dried over magnesium sulfate. The solvent was distilled off under reduced pressure. The residue was purified by subjecting to column chromatography filled with silica gel, to obtain 1.7 g. (yield: 58.6%) of the subject compound.

Melting point: 74°–75° C.

(3) Ethyl 6,7-dihydro-10-propyl-5,6,8,8-tetramethyl-8H-pyrano[3,2-g]chromone-2-carboxylate The sodium ethylate solution in ethanol was prepared from 0.5 g. of metallic sodium and 30 ml of ethanol. The ethanol solution, 1.5 g. of the compound obtained in (2) of Example 5 and 6 g. of diethyl oxalate were treated under the same condition as described in (3) of Example 1. There were thus obtained 1.34 g. (yield: 70%) of the subject compound.

Melting point: 46°–47° C.

Mass spectrum (m/e): 372 (M+).

Elementary analysis of the compound having presumed formula $C_{22}H_{28}O_5$ gave:

|  | C | H |
|---|---|---|
| Calculated (%): | 70.94 | 7.58 |
| Found (%): | 70.74 | 7.80 |

Infrared spectra $\nu_{max.}^{nuj.}$ cm$^{-1}$: 1725, 1650, 1620, 1260.

Nuclear magnetic resonance spectra (CDCl$_3$) δ: 0.94(t), 1.24(s), 1.46(s), 1.30(d), 2.76(s), 3.04–3.44(m), 6.88(s)

EXAMPLE 6

Ethyl 6,7-dihydro-5,7,8,8,10-pentamethyl-8H-pyrano[3,2-g]chromone-2-carboxylate (1) 7-Hydroxy-2,2,3,5,8-pentamethyl chroman 6.9 g. of 2,5-dimethyl resorcinol, 3 ml of concentrated sulfuric acid, 40 ml of isopropyl ether and 4.7 g. of 2,3-dimethyl-2-buten-1-ol were treated with procedures described in (1) of Example 5. There were thus obtained 2.9 g. of the subject compound.

(2) 6-Acetyl-7-hydroxy-2,2,3,5,8-pentamethylchroman

The procedures described in (2) of Example 5 were repeated except that the mixture was prepared from 2.6 g. of the compound obtained in (1) and 3.5 g. of boron trifluoride-acetic acid complex. There was thus obtained 2.0 g. (yield: 63.7%) of the subject compound.
Melting point: 87°–90° C.

(3) Ethyl 6,7-dihydro-5,7,8,8,10-pentamethyl-8H-pyrano[3,2-g]chromone-2-carboxylate A solution of sodium ethylate in ethanol was prepared from 1.0 g. of metallic sodium and 30 ml of ethanol. To this solution (40° C.), 2.0 g. of the compound obtained in (2) were added. Subsequently, 6 g. of diethyl oxalate were added dropwise at 50°–60° C. for 30 minutes to the mixture. After reflux for one hour, the reaction solution was poured into ice water, then acidified with hydrochloric acid and extracted with ether. The ether was distilled off from the extract. To the residue added a concentrated hydrochloric acid-containing ethanol, and the whole was refluxed for one hour. The ethanol was distilled off under reduced pressure. The residue was dissolved in ether, successively washed with water, aqueous 1 N sodium bicarbonate solution and again with water, then dried over magnesium sulfate. The ether was distilled off under reduced pressure. The residue was purified by subjecting to column chromatography filled with silica gel. There were thus obtained 1.7 g. (yield: 65.0%) of the subject compound.
Melting point: 141°–143° C.

Elementary analysis of the compound having presumed formula $C_{20}H_{24}O_5$ gave:

|  | C | H |
|---|---|---|
| Calculated (%): | 69.75 | 7.02 |
| Found (%): | 69.57 | 7.05 |

Mass spectra (m/e): 344 (M+).
Infrared spectra $\nu_{max.}^{nuj.}$ cm$^{-1}$: 1730, 1660, 1635, 1270.
Nuclear magnetic resonance spectra (CDCl$_3$) δ: 0.98(s), 1.38(s), 1.88–2.20(m), 2.16(s) 2.46(s), 6.88(s).

EXAMPLE 7

Ethyl 6,7-dihydro-10-ethyl-5,6,8,8-tetramethyl-8H-pyrano[3,2-g]chromone-2-carboxylate (1) 8-Ethyl-7-hydroxy-2,2,4,5-tetramethylchroman A mixed solution was prepared from 6.1 g. of 2-ethyl-5-methyl resorcinol, 40 ml of isopropyl ether and 2 ml of concentrated sulfuric acid. To this solution, 5.7 g. of 2-methylpentane-2,4-diol were added dropwise at about 60° C. for about 30 minutes. After cooling, this solution was successively washed with water, with aqueous 1 N sodium hydroxide solution and again with water, and then dried over magnesium sulfate. The solvent was distilled off under reduced pressure. The residue was purified by subjecting to column chromatography filled with silica gel. There were obtained 6.0 g. (yield: 64.1%) of the subject compound.

(2) 6-Acetyl-8-ethyl-7-hydroxy-2,2,4,5-tetramethylchroman

The procedures described in (2) of Example 5 were repeated except that the mixture was prepared from 4.68 g. of the compound obtained in (1) of Example 7 and 5.9 g. of boron trifluoride-acetic acid complex. The product was recrystallized from ether/n-hexane. There were obtained 3.0 g. (yield: 54.4%) of the subject compound.
Melting point: 70°–71° C.

(3) Ethyl 6,7-dihydro-10-ethyl-5,6,8,8-tetramethyl-8H-pyrano[3,2-g]chromone-2-carboxylate A solution of sodium ethylate in ethanol was prepared from 1.0 g. of metallic sodium and 30 ml of ethanol. The resulting solution, 2.76 g. of the compound obtained in (2) and 6 g. of diethyl oxalate were treated with the procedure described in (3) of Example 6. The product was recrystallized from ether/petroleum ether. There were obtained 1.9 g. (yield: 53.0%) of the subject compound.
Melting point: 71°–72° C.

Elementary analysis of the compound having presumed formula $C_{21}H_{26}O_5$ gave:

|  | C | H |
|---|---|---|
| Calculated (%): | 70.38 | 7.56 |
| Found (%): | 70.37 | 7.31 |

Mass spectrum (m/e): 358 (M+).
Infrared spectra $\nu_{max.}^{nuj.}$ cm$^{-1}$: 1725, 1655, 1630, 1260.
Nuclear magnetic resonance spectra (CDCl$_3$) δ: 1.24(s), 1.36(d), 1.48(s), 1.68–2.24(m), 2.76(s), 3.10–3.34(m), 6.88(s).

(4) Sodium 6,7-dihydro-10-ethyl-5,6,8,8-tetramethyl-8H-pyrano[3,2-g]chromone-2-carboxylate To 716 mg of the compound obtained in (3), were added 5 ml of ethanol. Subsequently, 2 ml of aqueous 1 N sodium hydroxide solution were added with stirring. Then, the procedures described in (4) of Example 1 were repeated. There were obtained 620 mg of the subject compound.
Melting point: over 250° C.

Elementary analysis of the compound having presumed formula $C_{19}H_{21}O_5Na$ gave:

|  | C | H |
|---|---|---|
| Calculated (%): | 64.77 | 6.01 |
| Found (%): | 64.75 | 6.04 |

Nuclear magnetic resonance spectra (CD₃OD) δ: 1.12(t), 1.20(s), 1.24(d), 1.64–2.24(m), 2.70(s), 2.70–3.04(m), 6.64(s).

Infrared spectra $\nu_{max}^{nuj.}$ cm$^{-1}$: 1625, 1575, 1140, 1120.

EXAMPLE 8

Ethyl 6,7-dihydro-10-methoxy-5,6,8,8-tetramethyl-8H-pyrano[3,2-g]chromone-2-carboxylate (1) 7,8-Dimethoxy-2,2,4,5-tetramethylchroman 8.4 g. of 2,3-dimethoxy-5-methylphenol, 7.0 g. of 2-methyl pentane-2,4-diol, 70 ml of isopropyl ether and 2 ml of concentrated sulfuric acid were treated with the same procedure as described in (1) of Example 7. There were obtained 8.4 g. (yield: 67.2%) of the subject compound.

(2) 7,8-Dihydroxy-2,2,4,5-tetramethylchroman

A mixed solution comprising 7.5 g. of the compound obtained in (1), 50 ml of acetic acid and 30 ml of 47% hydrobromic acid was refluxed for 5 hours, and concentrated under a reduced pressure. The concentrated solution was diluted with water and extracted with ether. The ether layer was successively washed with water, with aqueous 1 N sodium bicarbonate solution and again with water, and then dried over magnesium sulfate. The ether was distilled off. The residue was purified by subjecting to column chromatography filled with silica gel. There were obtained 3.0 g. (yield: 45.0%) of the subject compound.

(3) 6-Acetyl-7,8-dihydroxy-2,2,4,5-tetramethylchroman

The procedures described in (2) of Example 5 were repeated except that the mixture was prepared from 3.0 g. of the compound obtained in (2) of Example 8 and 7 g. of boron trifluoride-acetic acid complex. There were obtained 1.2 g. of the subject compound.

(4) Ethyl 6,7-dihydro-10-methoxy-5,6,8,8-tetramethyl-8H-pyrano[3,2-g]chromone-2-carboxylate A solution of sodium ethylate in ethanol was prepared from 0.5 g. of metallic sodium and 40 ml of ethanol. The resulting solution, 1.2 g. of the compound obtained in (3) and 6 g. of diethyl oxalate were treated with the procedures described in (3) of Example 1. To the resulting compound were added 20 ml of acetone, 2 g. of potassium carbonate, 2 g. of methyl iodide. The mixture was treated according to the procedure described in (4) of Example 3 to obtain 1.1 g. (yield: 67.5%) of the subject compound.

Melting point: 77°–78° C.

Mass spectrum (m/e): 360 (M+).

Elementary analysis of the compound having the presumed formula C₂₀H₂₄O₆ gave:

|  | C | H |
| --- | --- | --- |
| Calculated (%): | 66.65 | 6.71 |
| Found (%): | 66.77 | 6.83 |

Nuclear magnetic resonance spectra (CDCl₃)δ: 1.30(s), 1.34(d), 1.42(t), 1.52(s), 1.70–2.28(m), 2.74(s), 3.10–3.40(m), 7.92(s), 4.40(q), 6.88(s).

Infrared spectra $\nu_{max}^{nuj.}$ cm$^{-1}$: 1725, 1655, 1630, 1260.

EXAMPLE 9

Ethyl 6,7-dihydro-10-ethyl-6,8,8-trimethyl-8H-pyrano[3,2-g]chromone-2-carboxylate (1) 8-Ethyl-7-hydroxy-2,2,4-trimethyl chroman 6.9 g. of 2-ethyl resorcinol, 40 ml of isopropyl ether, 2 ml of concentrated sulfuric acid and 7.1 g. of 2-methylpentane-2,4-diol were treated with procedures described in (1) of Example 7. There was obtained 7.2 g. (yield: 65.5%) of the subject compound.

(2) 6-Acetyl-8-ethyl-7-hydroxy-2,2,4-trimethylchroman

The procedure described in (2) of Example 5 were repeated except that the mixture was prepared from 2.2 g. of the compound obtained in (1) of Example 9 and 6 g. of boron trifluoride-acetic acid complex. The product was further recrystallized from ether/n-hexane. There was obtained 1.6 g. (yield: 61.1%) of the subject compound.

Melting point: 104°–106° C.

(3) Ethyl 6,7-dihydro-10-ethyl-6,8,8-trimethyl-8H-pyrano[3,2-g]chromone-2-carboxylate A solution of sodium ethylate in ethanol was prepared from 0.46 g. of metallic sodium and 30 ml of ethanol. The resulting solution, 1.31 g. of the compound obtained in (2) and 6 g. of diethyl oxalate were treated according to the procedure described in (3) of Example 6. The product was recrystallized from ether/n-hexane. There were obtained 0.9 g. (yield: 53.3%) of the subject compound.

Melting point: 92°–93° C.

Mass spectrum (m/e): 344 (M+).

Elementary analysis of the compound having the presumed formula C₂₀H₂₄O₅ gave:

|  | C | H |
| --- | --- | --- |
| Calculated (%): | 69.75 | 7.02 |
| Found (%): | 69.46 | 7.07 |

Infrared spectra $\nu_{max}^{nuj.}$ cm$^{-1}$: 1735, 1650, 1630, 1260.

Nuclear magnetic resonance spectra (CDCl₃) δ: 1.24(s), 1.42(s), 1.50–2.00(m), 4.30(q), 6.84(s), 7.76(s).

EXAMPLE 10

Propyl 6,7-dihydro-6,8,8,10-tetramethyl-8H-pyrano[3,2-g]chromone-2-carboxylate A mixture solution was prepared from one gram of the compound obtained in (5) of Example 2, and 50 ml of n-propanol, and 0.5 ml of concentrated sulfuric acid. The mixed solution was refluxed for 3 hours. The n-propanol was distilled off under reduced pressure. The residue was dissolved in ether, subsequently washed with water, with aqueous 1 N sodium bicarbonate solution and again with water, and then dried over magnesium sulfate. The ether was distilled off. The product was recrystallized from ether/n-hexane solvent to obtain 0.8 g. of the subject compound.

Melting point: 144°–145° C.

Elementary analysis of the compound having presumed formula C₂₀H₂₄O₅ gave:

|  | C | H |
|---|---|---|
| Calculated (%): | 69.75 | 7.02 |
| Found (%): | 69.75 | 7.09 |

Mass spectrum (m/e): 344 (M+).

Infrared spectra $\nu_{max}.^{nuj.}$ cm$^{-1}$: 1730, 1650, 1630, 1270.

Nuclear magnetic resonance spectra (CDCl$_3$) δ: 1.04(t), 1.28(s), 1.40(d), 1.48(d), 2.30(s), 2.80–3.20(m), 4.30(t), 6.96(s), 7.90(s).

EXAMPLE 11

Butyl 6,7-dihydro-6,8,8,10-tetramethyl-8H-pyrano[3,2-g]chromone-2-carboxylate

1 Gram of the compound obtained in (5) of Example 2, 50 ml of n-butanol and 0.5 ml of concentrated sulfuric acid were treated under the same condition as in Example 10, to obtain 0.75 g of the subject compound.

Melting point: 134°–135° C.

Mass Spectrum (m/e): 358 (M+).

Elementary analysis of the compound having presumed formula C$_{21}$H$_{26}$O$_5$ gave:

|  | C | H |
|---|---|---|
| Calculated (%): | 70.37 | 7.31 |
| Found (%): | 70.42 | 7.31 |

Infrared spectra $\nu_{max}.^{nuj.}$ cm$^{-1}$: 1730, 1650, 1630, 1265.

Nuclear Magnetic Resonance spectra (CDCl$_3$) δ: 0.98(t), 1.28(s), 1.40(d), 1.48(s), 2.30(s), 2.80–3.20(m), 4.36(t), 6.96(s), 7.92(s).

EXAMPLE 12

Ethyl 6,7-dihydro-6-ethyl-8,8,10-trimethyl-8H-pyrano[3,2-g]chromone-2-carboxylate (1) 7-Hydroxy-2,2,8-trimethyl4-chromanone 42.7 Grams of 3-methyl crotonyl chloride were added dropwise at 45° C. for about 30 minutes to the mixture of 37.2 g. of 2-methyl resorsinol and 80 ml of boron trifluoride-ethyl ether complex with stirring. After stirring for 2 hours at about 60° C., the reaction mixture was poured into ice water and extracted with ether. The ether layer was washed, followed by extraction with 5% aqueous solution of sodium hydroxide. The layer of aqueous sodium hydroxide was recovered, acidified with hydrochloric acid, and then extracted with ether. After the ether layer was washed with water and dried over magnesium sulfate, the ether was distilled off under reduced pressure. The residue was recrystallized from ether/n-hexane to obtain 32.7 g. (yield: 52.9%) of the subject compound.

Melting point: 185°–187° C.

(2) 7-Benzoyloxy-2,2,8-trimethyl-4-chromanone

The mixture of 10.3 g. of the compound obtained in (1), 8.2 g. of benzyl chloride, 10.2 g. of potassium carbonate, 0.5 g. of potassium iodide, and 100 ml of acetone was refluxed for 2 hours. The mixture was then filtered, and the filtrate was concentrated. Ether was added to the concentrate. The ether layer was washed successively with water, 1 N aqueous sodium hydroxide, and again with water. The solution was dried over magnesium sulfate, and the solvent was distilled off under reduced pressure. The residue was recrystallized from ethyl acetate/n-hexane, to obtain 12.2 g. (yield: 82.4%) of the subject compound.

Melting point: 113° C.

(3) 7-Benzyloxy-2,2,8-trimethyl chromene

Grignard reagent was prepared by adding dropwise 7 g. of ethyl iodide to 1.1 g. of magnesium in 50 ml of ether. To the Grignard reagent were added 8.9 g. of the compound obtained in (2), at 15°–20° C. The mixture was stirred for 3 hours at room temperature. To the mixture was added aqueous solution of ammonium chloride. The whole was acidified with hydrochloric acid and extracted with ether. The ether layer was washed with water, and dried over magnesium sulfate. The solvent was distilled off under reduced pressure. The residue was purified by subjecting to column chromatography filled with silica gel, to obtain 6.3 g. (yield: 68.2%) of the subject compound.

(4) 4-Ethyl-7-hydroxy-2,2,8-trimethylchroman 6.3 Grams of the compound obtained in (3) wer subjected to catalytic reduction, using 0.5 g. of 10% palladium-carbon and 50 ml of ethanol under atmospheric pressure, to obtain 6.3 g. (yield: 56.1%) of the subject compound.

Melting point: 102°–103° C.

(5) 6-Acetyl-4-ethyl-7-hydroxy-2,2,8-trimethylchroman

The mixture of 2.2 g. of the compound obtained in (4) and 3 g. of boron trifluoride-acetic acid complex was stirred at 70° C. for 1.5 hours, poured into ice water and extracted with ethylacetate. The layer of ethyl acetate was successively washed with water, 1 N aqueous solution of sodium hydroxide, and again with water, and then dried over magnesium sulfate. The solvent was distilled off under reduced pressure. The residue was recrystallized from ether/n-hexane, to obtain 1.7 g. (yield: 64.9%) of the subject compound.

Melting point: 92°–93° C.

(6) Ethyl 6,7-dihydro-6-ethyl-8,8,10-trimethyl-8H-pyrano [3,2-g] chromone-2-carboxylate The ethanol solution of sodium ethylate was prepared from 0.5 g. of metallic sodium and 20 ml of ethanol. The ethanol solution, 1.31 g. of the compound obtained in (5) of Example 12 and 2.92 g. of diethyl oxalate were treated under thesame condition as described in (3) of Example 6. There were thus obtained 1.24 g. (yield: 72.1%) of the subject compound.

Melting point: 128°–130° C.

Mass spectrum (m/e): 344 (M+).

Elementary analysis of the compound having the presumed formula C$_{20}$H$_{24}$O$_5$ gave:

|  | C | H |
|---|---|---|
| Calculated (%): | 69.75 | 7.02 |
| Found (%): | 69.74 | 6.94 |

Infrared spectra $\nu_{max}.^{nuj.}$ cm$^{-1}$: 1730, 1650, 1625, 1115.

Nuclear magnetic resonance spectra (CDCl$_3$) δ: 0.94(t), 1.24(s), 1.48(s), 2.30(s), 4.40(q), 6.96(s), 7.92(s).

EXAMPLE 13

Ethyl 6,7-dihydro-8-propyl-6,8,10-trimethyl-8H-pyrano [3,2-g] chromone-2-carboxylate

(1) 7-Hydroxy-2,8-dimethyl-2-propyl-4-chromanone

To the mixture of 19.8 g. of 2-methyl resorcinol and 50 ml of boron trifluoride-ethyl ether complex were added dropwise 30 g. of 3-methyl-2-hexenoyl chloride with stirring at 45° C. for about 30 minutes. After stirring for 2 hours at about 60° C., the reaction mixture was poured into ice water, and extracted with ether. After washing with water, the ether layer was extracted with 5% aqueous solution of sodium hydroxide. After acidification with hydrochloric acid, the aqueous solution of sodium hydroxide was extracted with ether. The ether layer was washed with water, and dried over magnesium sulfate. The product was purified by subjecting to column chromatography filled with silica gel to obtain 26.1 g. (yield: 69.7%) of the subject compound as oily product.

(2) 7-Benzyloxy-2,8-dimethyl-2-propyl-4-chromanone

The mixture of 11.7 g. of the compound obtained in (1), 11.1 g. of benzyl bromide, 10.2 g. of potassium carbonate, and 100 ml of acetone was refluxed for 2 hours, followed by filtration. The filtrate was concentrated. Ether was added to the concentrate. The ether solution was washed successively with water, 1 N aqueous solution of sodium hydroxide, and again with water, and then dried over magnesium sulfate. The solvent was distilled off under reduced pressure. The residue was purified by subjecting to column chromatography filled with silica gel, to obtain 11.5 g. (yield: 91.0%) of the subject compound. Melting point: 45° C.

(3) 7-Benzyloxy-2,8-dimethyl-2-propylchromene

Grignard reagent was prepared by adding dropwise 8.52 g. of ethyl iodide to 70 ml of ether and 1.46 g. of magnesium. Said Grignard reagent and 9.72 g. of the compound obtained in (2) were treated in the same manner as described in (3) of Example 12, to obtain 6.5 g. (yield: 67.7%) of the subject compound as oily substance.

(4) 7-Hydroxy-2-propyl-2,4,8-trimethylchroman 6.5 Grams of the compound obtained in (3) were subjected to catalytic reduction with 0.5 g. of 10% palladium-carbon and 50 ml of ethanol under atmospheric pressure. The subject compound in amount of 4.0 g. (yield: 84.2%) was thus obtained.
Melting point: 60° C.

(5) 6-Acetyl-7-hydroxy-2-propyl-2,4,8-trimethylchroman

The mixture of 2.34 g. of the compound obtained in (4) and 2.93 g. of boron trifluoride-acetic acid complex was stirred at 70° C. for 1.5 hours, and poured into ice water, and followed by extraction with ethyl acetate. The extract was washed successively with water, 1 N aqueous solution of sodium hydroxide, and again with water, and then dried over magnesium sulfate. The solvent was distilled off under reduced pressure. The residue was purified by subjecting to column chromatography filled with silica gel, to obtain 2.3 g. (yield: 83.3%) of the subject compound.
Melting point: 73° C.

(6) Ethyl 6,7-dihydro-8-propyl-6,8,10-trimethyl-8H-pyrano [3,2-g] chromone-2-carboxylate The ethanol solution of sodium ethylate was prepared from 0.5 g. of metallic sodium and 20 ml of ethanol. The ethanol solution, 1.38 g. of the compound obtained in (5) of example 13, and 2.92 g. of diethyl oxalate were treated under the same condition as described in (3) of Example 6. There were thus obtained 1.24 g. (yield: 72.1%) of the subject compound.
Melting point: 85° C.
Mass spectrum (m/e): 358 (M+).
Elementary analysis of the compound having presumed formula $C_{21}H_{26}O_5$ gave:

|  | C | H |
|---|---|---|
| Calculated (%): | 70.37 | 7.31 |
| Found (%): | 70.26 | 7.28 |

Infrared spectra $v_{max.}^{nuj.}$ cm$^{-1}$: 1735, 1650, 1630, 1115.
Nuclear magnetic resonance spectra (CDCl$_3$) δ: 1.26(s), 1.40(s), 4.40(q), 6.96(s), 7.90(s).

EXAMPLE 14

Methyl 6,7-dihydro-6,8,8,10-tetramethyl-8H-pyrano [3,2-g] chromone-2-carboxylate The methanol solution of sodium methylate was prepared from 6.9 g. of metallic sodium and 200 ml of methanol. The methanol solution, 24.8 g. of the compound obtained in (2) of Example 2, and 35.4 g. of dimethyl oxalate were treated under the same condition as described in (3) of Example 6. There were thus obtained 24.7 g. (yield: 78.2%) of the subject compound.
Melting point: 150°-152° C.
Mass spectrum (m/e): 316 (M+).
Elementary analysis of the compound having the presumed formula $C_{18}H_{20}O_5$ gave:

|  | C | H |
|---|---|---|
| Calculated (%): | 68.34 | 6.37 |
| Found (%): | 68.25 | 6.40 |

Infrared spectra $v_{max.}^{nuj.}$ cm$^{-1}$: 1750, 1645, 1625, 1115.
Nuclear magnetic resonance spectra (CDCl$_3$) δ: 1.26(s), 1.36(d), 1.44(s), 2.28(s), 3.00(m), 3.94(s), 6.94(s), 7.90(s).

EXAMPLE 15

| Granules and tablets | |
|---|---|
| The compound obtained in 3) of Example 2 | 10 g. |
| Corn starch | 27.5 g. |
| Carboxymethylcellulose | 10 g. |
| Polyvinylpyrrolidone | 1.5 g. |

The compound obtained in (3) of Example 2 was homogeneously mixed with corn starch and carboxymethylcellulose. To the mixture, the ethanol solution of polyvinylpyrrolidone was added and granulated. To the resulting granules was added 1 g. of calcium stealate.

Said mixture was compressed to obtain the desired tablets weighing 50 mg. per tablet.

EXAMPLE 16

| Powder and capsules | |
| --- | --- |
| The compound obtained in 3) of Example 7 | 20 g. |
| Crystallized cellulose | 280 g. |

The above two ingredient were blended to prepare the powder. The capsules were prepared by packing said powder in No. 3 Hard Gelatin Capsule.

EXAMPLE 17

| Syrup | | |
| --- | --- | --- |
| The compound obtained in 4) of Example 2 | 0.5 | g. |
| Methylcellulose | 2 | g. |
| White sugar | 20 | g. |
| Essence of strawberry | 0.1 | ml |
| Methylparaben | 0.1 | g. |
| Distilled water | balance | |
| Total volume | 100 | ml |

To methylcellulose were added 50 ml of distilled water to obtain the mixture. To said mixture were added the compound obtained in (4) of Example 2, white sugar, essence of strawberry, and methylparaben, and the whole was mixed altogether. Distilled water was added to the mixture, so that the total volume may become 100 ml. The desired syrup was thus produced.

What is claimed is:

1. A pyranochromone derivative having the general formula:

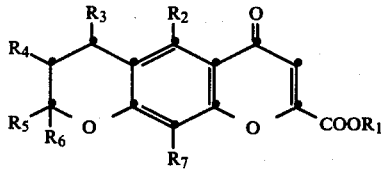

wherein $R_1$ represents hydrogen atom, an alkali metal or an alkyl group containing 1-4 carbon atoms; $R_2$, $R_3$ and $R_4$ represent hydrogen atom or an alkyl group containing 1-4 carbon atoms respectively, provided that both $R_3$ and $R_4$ are not hydrogen atom at the same time; $R_5$ and $R_6$ represent an alkyl group containing 1-4 carbon atoms respectively; and $R_7$ represents hydrogen atom, hydroxyl group, an alkyl group containing 1-4 carbon atoms or an alkoxyl group containing 1-4 carbon atoms.

2. The derivative according to claim 1, wherein said derivative is ethyl 6,7-dihydro-5,6,8,8,10-pentamethyl-8H-pyrano [3,2-g] chromone-2-carboxylate.

3. The derivative according to claim 1, wherein said derivative is sodium 6,7-dihydro-5,6,8,8,10-pentamethyl-8H-pyrano [3,2-g] chromone-2-carboxylic.

4. The derivative according to claim 1, wherein said derivative is ethyl 6,7-dihydro-6,8,8,10-tetramethyl-8H-pyrano [3,2-g] chromone-2-carboxylate.

5. The derivative according to claim 1, wherein said derivative is sodium 6,7-dihydro-6,8,8,10-tetramethyl-8H-pyrano [3,2-g] chromone-2-carboxylate.

6. The derivative according to claim 1, wherein said derivative is 6,7-dihydro-6,8,8,10-tetramethyl-8H-pyrano [3,2-g] chromone-2-carboxylic acid.

7. The derivative according to claim 1, wherein said derivative is ethyl 6,7-dihydro-10-methoxy-6,8,8-trimethyl-8H-pyrano [3,2-g] chromone-2-carboxylate.

8. The derivative according to claim 1, wherein said derivative is sodium 6,7-dihydro-10-methoxy-6,8,8-trimethyl-8H-pyrano 3,2-g] chromone-2-carboxylate.

9. The derivative according to claim 1, wherein said derivative is ethyl 6,7-dihydro-10-ethoxy-6,8,8-trimethyl-8H-pyrano [3,2-g] chromone-2-carboxylate.

10. The derivative according to claim 1, wherein said derivative is ethyl 6,7-dihydro-10-hydroxy-6,8,8-trimethyl-8H-pyrano [3,2-g] chromone-2-carboxylate.

11. The derivative according to claim 1, wherein said derivative is ethyl 6,7-dihydro-10-propyl-5,6,8,8,-tetramethyl-8H-pyrano [3,2-g] chromone-2-carboxylate.

12. The derivative according to claim 1, wherein said derivative is ethyl 6,7-dihydro-5,7,8,8,10-pentamethyl-8H-pyrano [3,2-g] chromone-2-carboxylate.

13. The derivative according to claim 1, wherein said derivative is ethyl 6,7-dihydro-10-ethyl-5,6,8,8-tetramethyl-8H-pyrano [3,2-g] chromone-2-carboxylate.

14. The derivative according to claim 1, wherein said derivative is sodium 6,7-dihydro-10-ethyl-5,6,8,8-tetramethyl-8H-pyrano [3,2-g] chromone-2-carboxylate.

15. The derivative according to claim 1, wherein said derivative is ethyl 6,7-dihydro-10-methoxy-5,6,8,8-tetramethyl-8H-pyrano [3,2-g] chromone-2-carboxylate.

16. The derivative according to claim 1, wherein said derivative is ethyl 6,7-dihydro-10-ethyl-6,8,8-trimethyl-8H-pyrano [3,2-g] chromone-2-carboxylate.

17. The derivative according to claim 1, wherein said derivative is propyl 6,7-dihydro-6,8,8,10-tetramethyl-8H-pyrano [3,2-g] chromone-2-carboxylate.

18. The derivative according to claim 1, wherein said derivative is butyl 6,7-dihydro-6,8,8,10-tetramethyl-8H-pyrano [3,2-g] chromone-2-carboxylate.

19. The derivative according to claim 1, wherein said derivative is ethyl 6,7-dihydro-6-ethyl-8,8,10-trimethyl-8H-pyrano [3,2-g] chromone-2-carboxylate.

20. The derivative according to claim 1, wherein said derivative is ethyl 6,7-dihydro-8-propyl-6,8,10-trimethyl-8H-pyrano [3,2-g] chromone-2-carboxylate.

21. The derivative according to claim 1, wherein said derivative is methyl 6,7-dihydro-6,8,8,10-tetramethyl-8H-pyrano [3,2-g] chromone-2-carboxylate.

22. A therapeutic composition which comprises an anti-allergically effective amount of a pyranochromone derivative having the general formula:

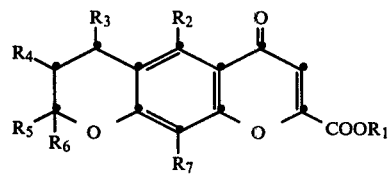

wherein $R_1$ represents hydrogen atom, an alkali metal or an alkyl group containing 1-4 carbon atoms; $R_2$, $R_3$ and $R_4$ represent hydrogen atom or an alkyl group containing 1-4 carbon atoms respectively, provided that both $R_3$ and $R_4$ are not hydrogen atom at the same time; $R_5$ and $R_6$ represent an alkyl group containing 1-4 carbon atoms respectively; and $R_7$ represents hydrogen atom, hydroxyl group, an alkyl group containing 1-4 carbon atoms or an alkoxy group containing 1–4 carbon atoms in admixture with an orally acceptable pharmaceutical carrier therefor.

23. A therapeutic composition according to claim 22, wherein said derivative is ethyl 6,7-dihydro-6,8,8,10-tetramethyl-8H-pyrano[3,2-g]chromone-2-carboxylate.

24. A therapeutic composition according to claim 22, wherein said derivative is sodium 6,7-dihydro-6,8,8,10-tetramethyl-8H-pyrano[3,2-g]chromone-2-carboxylate.

25. A therapeutic composition according to claim 22, wherein said derivative is 6,7-dihydro-6,8,8,10-tetramethyl-8H-pyrano[3,2-g]chromone-2-carboxylic acid.

26. A therapeutic composition according to claim 22, wherein said derivative is ethyl 6,7-dihydro-5,7,8,8,10-pentamethyl-8H-pyrano[3,2-g]chromone-2-carboxylate.

27. A therapeutic composition according to claim 22, wherein said derivative is ethyl 6,7-dihydro-10-methoxy-6,8,8-trimethyl-8H-pyrano[3,2-g]chromone-2-carboxylate.

28. A therapeutic composition according to claim 22, wherein said derivative is ethyl 6,7-dihydro-10-ethyl-5,6,8,8-tetramethyl-8H-pyrano[3,2-g]chromone-2-carboxylate.

* * * * *